United States Patent [19]
Roberts et al.

[11] Patent Number: 5,741,177
[45] Date of Patent: Apr. 21, 1998

[54] TISSUE SAMPLING AND ANALYSIS

[75] Inventors: Denis William Roberts, Shelley; David Steven Woodhouse, Byford; David Pethick, Hamilton Hill; John Christian Bensink, Brisbane, all of Australia

[73] Assignee: Meat Research Corporation, Sydney, Australia

[21] Appl. No.: 495,981

[22] Filed: Jun. 28, 1995

[30] Foreign Application Priority Data

Jun. 28, 1994 [AU] Australia .................. PM6477
Mar. 17, 1995 [AU] Australia .................. PN1803

[51] Int. Cl.$^6$ .................................................. A22B 5/00
[52] U.S. Cl. ........................................ 452/198; 83/919
[58] Field of Search ............................ 452/198; 83/919

[56] References Cited

U.S. PATENT DOCUMENTS

| | | | |
|---|---|---|---|
| 3,683,892 | 8/1972 | Harris | 30/380 |
| 4,226,540 | 10/1980 | Barten et al. | 356/445 |
| 4,407,833 | 10/1983 | Swartz | 426/281 |
| 5,168,102 | 12/1992 | Cogburn | 514/2 |
| 5,470,597 | 11/1995 | Mendenhall | 426/521 |
| 5,489,443 | 2/1996 | Knipe et al. | 426/264 |

FOREIGN PATENT DOCUMENTS

| | | |
|---|---|---|
| 237884 | 3/1962 | Australia . |
| 3430910A1 | 3/1985 | Germany . |
| 553 970 | 11/1975 | U.S.S.R. . |

Primary Examiner—Willis Little
Attorney, Agent, or Firm—Drummond & Duckworth

[57] ABSTRACT

Obtaining an early indication of the quality of meat such as defective meat comprising the steps of taking a sample of muscle tissue, disrupting and incubating the sample in order to activate and progress the conversion of glycogen to lactic acid so that the conversion proceeds at a rapid rate by comparison to normal conversion rate in muscle tissue processed and stored normally in meat processing operations and providing an indication of the pH to determine if in range that indicates the meat is defective. A sampling tool (111) usable to sample a muscle tissue having a conical tool head (112) with a leading point (121) to aid insertion into an animal and rearwardly facing cutting edge (123) that takes a sample of tissue when the tool is being withdrawn. A sample removing means (127) having a front convex surface (128) able to force the sample out of a concave base (120) of the tool head (112).

19 Claims, 3 Drawing Sheets

TISSUE SAMPLING AND ANALYSIS

BACKGROUND OF THE INVENTION

In order to increase the quality of meat for domestic use and for export, it is necessary to test carcass meat so that contaminated and low quality meat can be identified and rejected and so that meat processing can be improved. One particular test is to identify "dark cutting" meat, also known as dark-firm-dry, or DFD meat. Another test is for early detection of "pale-soft-exudative" or PSE meat in pigs which results from the rapid development of a low pH (less than about 6.0) soon after slaughter.

Dark cutting or DFD meat is a quality defect found in many meat species, including beef and sheep. The condition is associated with a pH higher than 5.8, and particularly higher than 6, in the meat about 24 or more hours after slaughter. The condition arises from a low concentration of glycogen in the muscles at the time of slaughter leading to a reduced lactic acid content in the meat some time after slaughter when the ultimate pH level of the muscles has stabilised. The reduction in concentrations of glycogen is caused by stress in the animals leading up to slaughter.

Detection of DFD meat can be readily carried out after chilling and storage of a carcass for, say, 24 hours or more. In hot boning of freshly slaughtered animal carcasses the meat is packed and is therefore desirably classified according to its quality at a very early stage, before any dark colour will have developed. Because the meat will not have developed its ultimate pH in such hot boning practices, pH testing cannot provide a basis for early detection of DFD meat.

In many testing procedures including detection of DFD or PSE meat, it is necessary to take a sample of carcass meat. In abattoirs fast processing is desirable for economic and quality reasons and therefore, it is desirable that a sample be taken quickly and cheaply.

It is an object of a first aspect of the present invention to provide a process and apparatus for reliably detecting defective meat at a relatively early stage, normally after animal slaughter.

It is an object of a second aspect of the invention to provide a sampling tool which is able to take a sample of carcass meat simply and economically.

It is a preferred object of the second aspect to provide a sampling tool which is able to obtain an animal tissue sample of in the order of 1 cc or of the order of magnitude of 1 gm of carcass meat.

SUMMARY OF THE INVENTION

In a first aspect of the invention there is provided a process for obtaining an early indication of the quality of meat such as defective meat, the process comprising the steps of taking a sample of muscle tissue from an animal, disrupting the sample of muscle tissue so as to activate and accelerate the conversion of glycogen to lactic acid and achieve an accelerated reduction of the pH, incubating the sample after the disrupting step at a temperature to progress the conversion of glycogen to lactic acid, and providing an indication of the pH of the tissue sample after incubation.

The step of disrupting the sample of muscle tissue may comprise freezing the sample, and, if desired, also pulverising the sample while it is frozen. Alternatively, the step of disrupting the sample of muscle tissue may comprise homogenising the sample. As a further alternative, the step of disrupting the sample of muscle tissue may comprise pulverising the sample at about 1500 psi.

The step of incubating the sample is preferably carried out at or above room temperature, e.g., by placing the sample in a vessel which is immersed in a water bath at up to 43° C.

Preferably all the steps of the process are carried out within fifteen minutes.

According to a second aspect of the invention there is provided a sampling tool for taking a sample of animal tissue, such as carcass meat, comprising a tool head having a sharp end able to be inserted into the animal tissue, and a sampling edge positioned to face rearwardly relative to the sharp end such that, upon insertion of the tool head into the animal tissue, the sampling edge follows the sharp end, and upon retraction of the tool head, the sampling edge takes a sample of tissue from the animal. The sample can be recovered from the tool head when the tool head is fully withdrawn.

Preferably the tool head has a substantially conical shape with the point of the conical tool head forming the sharp end. In this embodiment, the circular base of the cone may have its outer circular circumference of the circular base forming the sampling edge. This base may be concave at its outer circumference to sever the sample of animal tissue as the tool head is retracted. However, the sampling edge may if desired take other forms. For example, the sampling edge may be curved to extend only part of the way around the tool head. If desired, there may be provided several sampling edges facing rearwardly so that the head in longitudinal cross section has a saw-tooth profile. The sampling edge is able to cut, scrape or otherwise sample a piece of carcass meat upon extraction of the tool head.

In one form of the invention the tool head has one end of a support shaft fixed thereto. In the preferred embodiment the shaft is fixed to the circular base of the tool head, and the outer or free end of the shaft is provided with a handle. The handle may be either a pistol-grip handle and may extend transversely to the shaft, or may be a handle coaxial with the shaft.

A sample removing means may be provided for assisting removal of the sample from the sampling tool, e.g., by squeezing the sample to extrude out from the sampling edge. The sample removing means may comprise a collar which encircles and slides along the shaft. The collar may have a front face shaped to complement the concave shape of the circular base of the conical head so that by sliding the collar along the shaft, the convex shape of the front face of the collar engages the concave surface of the circular base and extrudes the sample of carcass meat radially outwardly off the sampling tool. The sample may be recovered in any convenient manner, e.g., by a suction tube.

In one possible embodiment, the sample removing collar may include a cutting edge which faces forwardly towards the tool head and extends radially out from the shaft and is able to cut any sinew or gristle or the like to ensure the sample does not remain encircles around the shaft. A notch is provided extending radially along the concave surface of the circular base complementary to the shape of the cutting edge for engagement of the cutting edge in the notch when the collar's convex surface engages the concave surface of the base.

BRIEF DESCRIPTION OF THE DRAWINGS

Possible and preferred features of the present invention will not be described with particular reference to the accompanying drawings. However, it is to be understood that the features illustrated in and described with reference to the drawings are not to be construed as limiting the scope of the invention. In the drawings.

DETAILED DESCRIPTION

Figure 1:
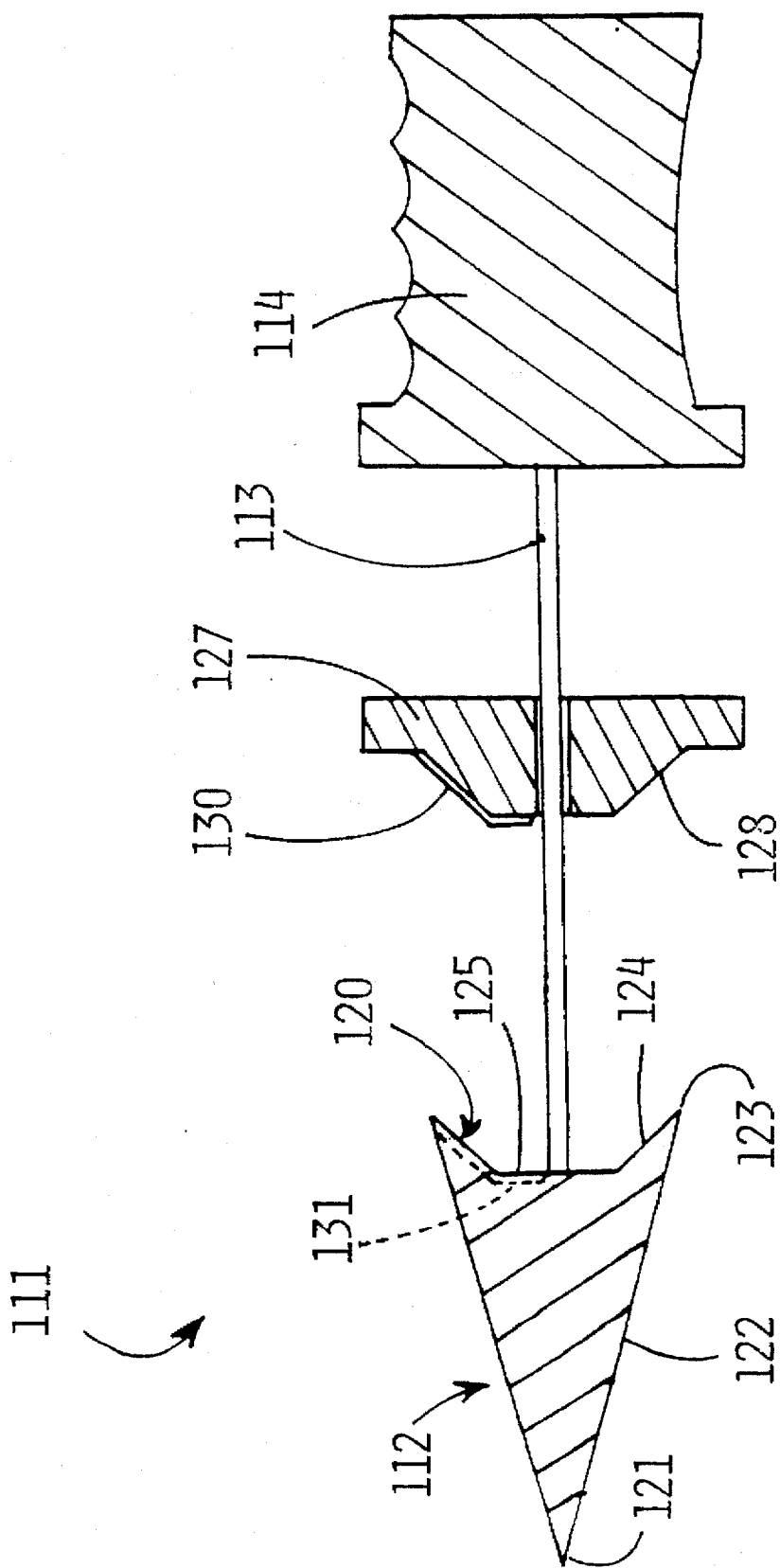
FIG. 1 is a side sectional view of a sampling tool in accordance with an embodiment of the invention.

Referring to FIG. 1 a sampling tool 111 is shown having a circular support shaft 113 which at one end is attached to a handle 114 encircling the end of the shaft and coaxially aligned with the shaft. The other end of the shaft is connected to a tool head 112.

The tool head 112 has a substantially conical shape coaxially mounted on the end of the shaft 113 with the sharp point or tip 121 of the conical tool head 112 pointing away from and being aligned with the shaft 113.

The external surface of the tool head 112 comprises a conical surface 122 extending from the point 121 to a base 120 having a circular cicumferential base edge 123. The base 120 has a concave shape defined by a frusto conical surface 124 which extends inwardly from the circular base edge 123 at an acute angle to the conical surface 122 and a flat annular surface 125 orthogonal to the axis of the shaft 113 and through which the shaft 113 passes to mount the head 112. The sharp point 121 and conical surface 122 enable insertion of the sampling head 112 into the animal tissues, particularly carcass meat, to be sampled. The position and orientation of the circular base edge 123 allows it to easily follow the point 121 of the tool head 112 into the carcass meat. The acute angle between the frusto conical surface 124 and the conical surface 122 enables the circular base edge 123 to act as a scraping or cutting edge which is able to cut or scrape tissues from the carcass meat when the sampling head 112 is retracted from the carcass meat. The configuration of the base 120 and the circular base edge 123 enables the tissue sample scraped away to be retracted from the animal carcass when the sampling tool 111 is retracted.

A collar 127 is mounted on the shaft 113 so that it can slide along the shaft in order to remove the sample from the sampling head 112. The collar 127 includes a convex surface 128 which is complementary to the shape of the concave base 120. By sliding the collar 127 so that the convex surface 128 engages the concave base 120 of the tool head 112, the sampled carcass meat is squeezed or extruded out to facilitate recovery of the sample.

The sample removing collar 127 includes a cutting edge 130 which faces forwardly towards the tool head 112 and extends radially out from the shaft 113. The edge 130 cuts any sinew or gristle or the like to ensure the sample does not remain encircled around the shaft 113. A notch 131 extends radially along the concave surface 120 of the circular base complementary to the shape of the cutting edge 130 so that the cutting edge 130 engages in the notch 131 to cut sinew etc. when the collar's convex surface 128 engages the concave base surface 120 of the head 112.

In one possible embodiment of the invention useful for taking tissue samples of about or less than 1 gm from beef carcasses, the length of the conical tool head 112 may be about 23 mm and the diameter of the circular base edge 123 may be 13 mm. The preferred embodiment of the sampling tool described and illustrated can be readily and quickly cleaned by water jet and sterilised by immersion in hot water prior to a subsequent sampling operation.

It should be evident from the preceding description and drawing that the preferred embodiment of the sampling tool according to the present invention is simple and can be used effectively to take animal tissue samples, is simple to manufacture, and can be readily cleaned and sterilised. The tool may also be used or modified for use with other animals such as pigs, sheep or deer, particularly in relation to the processing of animals in the meat industry.

The tissue sampling tool can be of particular use in the detection of DFD or PSE meat. A process according to the second aspect of the invention suitable for obtaining an early indication of the quality of meat such as dark cutting or DFD meat comprises the steps of taking a sample of muscle tissue from an animal, disrupting the sample of muscle tissue so as to activate and accelerate the conversion of glycogen to lactic acid and achieve an accelerated reduction of the pH, incubating the sample after the disrupting step at a temperature to progress the conversion of glycogen to lactic acid, and providing an indication of the pH of the tissue sample after incubation.

This process has been found to provide a reliable indication of the ultimate pH of the animal muscle from which the tissue sample was taken after the carcass has been hung in a conventional chiller for in excess of 24 hours. Thus the indication of pH obtained by the process, if more than about 5.8, and more particularly more than 6.0, will provide a good indicator of dark cutting or DFD meat.

The process and individual steps described in more detail in this specification will be described in relation to processing of beef, however the sampling tool and process of detection is applicable to other animals, particularly including sheep (for DFD meat) and pigs (for detecting PSE meat). The process may also be used to detect good quality or other quality meat as provided by the indicated pH being in a particular range.

The sample is taken generally at the time or relatively soon after slaughter so that DFD meat can be identified at a very early stage. It may even be possible to take a tissue sample from a live animal proposed to be slaughtered so that if the animal has an excessively low glycogen level in its muscle tissue, the animal may be separated for a period of rest and normal feedings so as to enable the animal to recover from its stress induced condition prior to slaughter. In a conventional abattoir, the muscle tissue sample could be taken from a carcass at the legging station where the preliminary manual dressing operation of opening the hide is carried out. This stage would be normally less than ten minutes after slaughter.

The muscle from which the tissue sample is taken may be the m. semitendinosis (or "ST" muscle). The ST muscle is a type IIB muscle which in a healthy unstressed animal has a lower glycogen concentration than, for example, m. longissimus dorsi, a muscle classified as type IIA, so that the ST muscle would appear to need depletion by a lesser amount to show a positive test for DFD meat. Also, the ST muscle lays superficially on the rump and below the tail of the animal and is readily accessible at the legging station and is also readily distinguishable from other muscles in the same vicinity.

The taking of the muscle tissue sample may be a manual operation and may be carried out using any conventional or convenient instrument for taking tissue samples for biopsy. The sampling tool described in relation to FIG. 1 is particularly suitable. The taking of the sample may be automated, for example by mechanically detecting and determining the position of the rump, or by image analysis of the carcass to determine its position, and hence determine the location of the ST muscle. A sampling tool in the form of a probe may then be automatically advanced and positioned to take the sample, then retracted and the sample deposited for further processing.

The size of the sample taken in experimental procedures included samples ranging from 3 gm to 10 gm and these sample sizes were adequate for effective indication of DFD meat. Sample sizes as small as 1 gm or less can be taken without compromising the reliability of the indication.

The step of disrupting the muscle tissue sample has the aim of activating the conversion of glycogen to lactic acid so that it proceeds at a rapid rate by comparison to the normal conversion rate in muscle tissues in a carcass or carcass section processed and stored normally in meat processing operations.

The main factors stimulating rapid glycogen breakdown are an active glycogen phosphorylase and a need for energy by the cell—the latter can be translated into low ATP and high ADP concentrations. Muscle tissue disruption should ensure that glycogen phosphorylase is in the active form since it is strongly activated by glycogen phosphorylase kinase under the influence of calcium. Calcium levels would be increased due to tissue disruption as they normally reside within the mitochondria and endoplasmic reticulum. The concentration of ADP should be high in disrupted muscle tissue since dispersed myofilaments would result in a very strong actinomyosin ATP'ase.

The step of disrupting the muscle tissue may comprise homogenisation of the muscle tissue sample, or freezing and subsequent thawing (with or without pulverisation of the frozen sample prior to thawing), or pressurisation of the sample.

Homogenisation, e.g. for thirty seconds, in a conventional laboratory homogeniser is one possible method of disrupting the muscle tissues. However homogenisation may not be the optimum process since experiments showed that homogenisation led to a higher indicated pH at the end of the incubation process which was a less accurate indicator of the actual ultimate pH of the muscle from which the sample was taken compared to the freezing or pressure treatment processes.

The second possible disrupting process may comprise freezing the sample e.g., by immersing a receptacle containing the sample in liquid nitrogen, or exposing the sample to carbon dioxide snow. The freezing of the tissue disrupts cell structure including cell membranes so that when the sample is subsequently thawed, the glycogen conversion to lactic acid is accelerated. When the sample is frozen, it is possible to also pulverise the sample to further assist in disruption of the muscle tissues although this step has been found to be unnecessary since frozen and thawed tissue samples also display accelerated glycogen conversion.

A further possible process for disrupting muscle tissues may comprise subjecting the sample to high pressure. An experimental sample of approximately 3–5 gm of fresh muscle was wrapped in "cling wrap" (of the kind used for packaging of food products in commercial and domestic food processing). The sample was then placed in a solution of oil within a pressure vessel and pressure of 14,000 psi was applied for a predetermined time. The tissue was then removed and the sample was incubated and the pH monitored. Pressure treatment for less than about a minute did not promote rapid glycogen conversion to achieve rapid reduction of pH, however when the pressure was applied for five minutes or more, the pH changed more rapidly and the indicated pH more closely approached the ultimate pH of the muscle from which the sample was taken. Therefore pressure treatment for about five minutes or greater than five minutes is preferred.

Preferably the disrupted muscle tissue sample is not diluted since tests indicated that dilution retarded the rate of glycogen conversion.

The next step of incubating the disrupted muscle tissue sample may comprise a conventional process of allowing the sample to stand so that the glycogen within the sample is converted to lactic acid. Preferably the temperature of the incubation is controlled so as to enable uniform conditions to be applied for helping to optimise accuracy of results and enable true comparisons of multiple testing operations. The incubation may be carried out with the sample in a vessel immersed, for example, in a water bath at a predetermined temperature. Tests have been carried out by incubating samples in a water bath at 43° C. with satisfactory results. Also samples have been incubated at room temperature (about 23° C.) with satisfactory results.

The period of incubation can be empirically determined. Incubation of samples that have undergone freezing and thawing (both with and without pulverisation when frozen) showed a stable pH being reached after about ten minutes of incubation and this pH was a reliable indicator of the ultimate pH of the muscle from which the sample was taken. In the case of the pressure treated tissue sample, incubation for five minutes appeared sufficient for the pH to reduce to a stable level which was a reliable indicator of the ultimate pH of the muscle from which the sample was taken.

The step of indicating the pH may comprise measuring the pH, e.g. using a conventional pH meter, having traditional glass electrode. The electrodes can be regularly calibrated and adjustments made for temperature variations. In the experimental stages, measurement of pH is desirable to more accurately monitor and test the process. However in a commercial meat testing operation, it may be sufficient for a simple indication to be given whether the pH exceeds a predetermined level or not. In particular, a simple indication may be needed whether a particular muscle tissue sample has after disruption and incubation reached a stable pH of greater than about 5.8, or particularly greater than 6.0, thereby indicating that the meat of the carcass from which that sample was taken is likely to be dark cutting or DFD meat. Any suitable pH indicator dye which changes colour at, say, pH 6.0 may therefore be used to indicate the pH and therefore enable classification of the meat.

EXAMPLE 1

Figure 2:
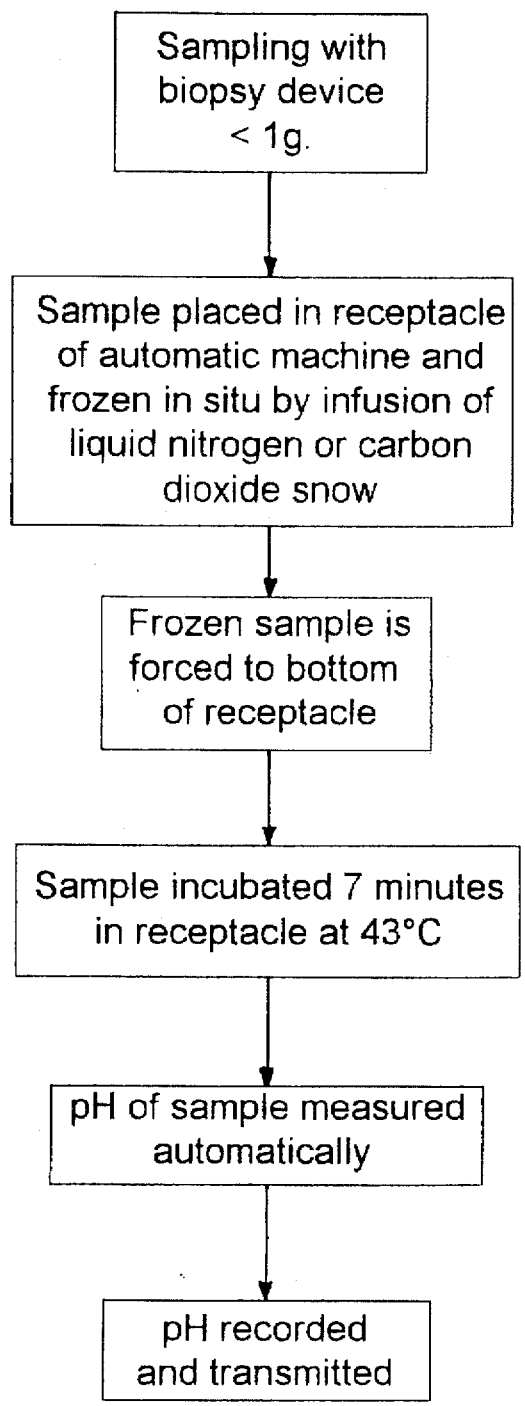
FIG. 2 is a flow diagram of a first method of analysis of a sample which may be taken with the sampling tool of FIG. 1.

One particularly tested procedure involving freezing and incubation but not pressure treatment is shown in FIG. 2 and comprises the following steps:

i. A 'biopsy' sample of 0.2 gm to 1 gm is taken manually by use of the disclosed sampling tool or other sampling means.

ii. A suction cup or tube of the measuring instrument recovers the sample from the tool and with a puff of air under positive pressure deposits the sample in a receptacle where it is frozen instantly by infusion of liquid nitrogen or carbon dioxide snow.

iii. A piston forces the frozen sample to the bottom of the receptacle which may slightly squash the sample but does not crush or otherwise apply pressure treatment to the sample.

iv. the sample is then incubated by immersion of the receptacle in a water bath at a temperature of 42° C. to 43° C. for a period of seven minutes. The piston and receptacle walls transfer heat from the bath to the sample.

v. The pH of the sample is then automatically read by a pH meter.

vi. The measured pH is recorded and transmitted as required.

EXAMPLE 2

Figure 3:
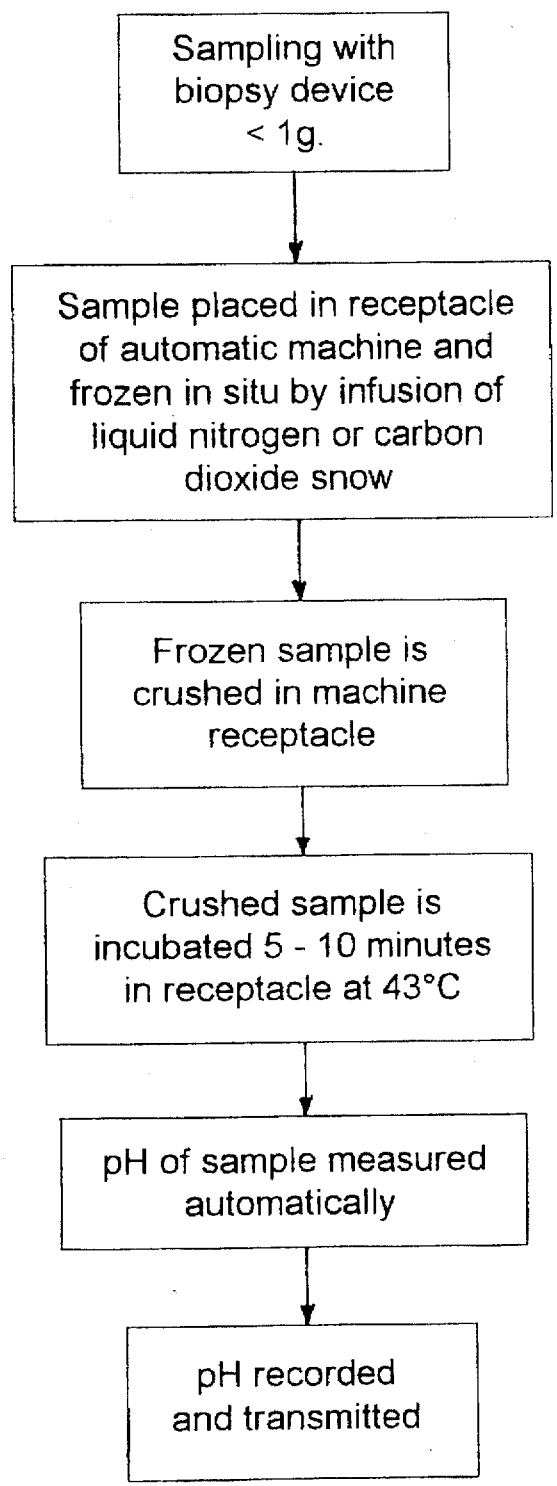
FIG. 3 is a flow diagram of a second method of analysis of a sample.

A combination procedure involving both freezing and pressure treatment could be used. The complete procedure could be as shown in FIG. 3 and as follows:

i A 'biopsy' sample of less than 1 gm could be semi-automatically taken and placed in a small stainless alloy receptacle and frozen in situ by an application of liquid nitrogen or carbon dioxide snow.

ii A precisely fitting piston at the same temperature is then forced onto the frozen meat sample in the receptacle to pulverise or crush it with appropriate force. The force is of the order of 15000 psi. The piston could maintain the pressure for a period if required. This crushing would give additional breakdown of find muscle structures, would result in even heat transfer and ensure that the small sample was correctly presented to the pH probe at the completion of incubation.

iii. The meat sample, still in its receptacle would then be incubated at 43° C. for the required time, indicatively five to ten minutes.

iv. The pH of the sample is then automatically measured, recorded and transmitted as required.

It will be seen that the preferred processes particularly described herein can be implemented so as to enable indication of dark cutting of DFD meat within about fifteen minutes, i.e., the total of the times taken for sampling, muscle disrupting, incubation and pH indication. Indication of DFD meat within fifteen minutes would be a time frame well before the carcass was processed through the slaughter room operations so that a carcass having DFD meat could be routed for different handling or processing operations.

It is to be understood that various alterations, modifications and/or additions may be made to the features of the possible and preferred embodiment(s) of the invention as herein described without departing from the scope of the invention.

We claim:

1. A process for obtaining an early indication of the quality of meat such as defective meat, the process comprising the steps of:

taking a sample of muscle tissue from an animal, disrupting the sample of muscle tissue so as to activate and accelerate the conversion of glycogen to lactic acid and achieve an accelerated reduction of the pH, incubating the sample after the disrupting step at a temperature to progress the conversion of glycogen to lactic acid, and providing an indication of the pH of the tissue sample after incubation.

2. A process as defined in claim 1 wherein the step of disrupting the sample of muscle tissue comprises freezing the sample.

3. A process as defined in claim 2 wherein the step of disrupting the sample further comprises pulverising the sample while it is frozen.

4. A process as defined in claim 1 wherein the step of disrupting the sample of muscle tissue comprises homogenising the sample.

5. A process as defined in claim 1 wherein the step of disrupting the sample of muscle tissue comprises pulverising the sample.

6. A process as defined in claim 2 wherein the step of disrupting the sample of muscle tissue comprises pulverising the sample.

7. A process as defined in claim 1 wherein the step of incubating the sample is carried out at or above room temperature.

8. A process as defined in claim 7 wherein the step of incubating the sample comprises placing the sample in a vessel which is immersed in a water bath at about 43° C.

9. A process as defined in claim 2 wherein the step of incubating the sample comprises placing the sample in a vessel which is immersed in a water bath at about 43° C.

10. A process as defined in claim 1 wherein the steps of the process are carried out within fifteen minutes.

11. A sampling tool for taking a sample of animal tissue, such as carcass meat, comprising a tool head having a sharp end able to be inserted into the animal tissue, a sampling edge positioned to face rearwardly relative to the sharp end and a remainder portion of the sampling tool including the portion of the sampling tool insertable into the animal tissue extending rearwardly from said sampling edge, said sampling edge projecting outward substantially beyond said remainder portion of the sampling tool such that, upon insertion of the tool head into the animal tissue, the sampling edge follows the sharp end, and upon retraction of the tool head, the sampling edge takes a sample of tissue from the animal.

12. A sampling tool as defined in claim 11 wherein the tool head is substantially conical, with the point of the conical tool head forming the sharp end of the tool head.

13. A sampling tool as defined in claim 11, wherein the tool head has a base facing rearwardly relative to the sharp end, the base having a outer circumference forming the sampling edge.

14. A sampling tool as defined in claim 12, wherein the tool head has a base facing rearwardly relative to the sharp end, the base having a outer circumference forming the sampling edge.

15. A sampling tool as defined in claim 13, wherein the base is concave at its outer circumference such that the sample is severed from the animal tissue as the tool head is retracted and the sample is withdrawn in the concave base.

16. A sampling tool as defined in claim 14, wherein the base is concave at its outer circumference such that the sample is severed from the animal tissue as the tool head is retracted and the sample is withdrawn in the concave base.

17. A sampling tool as defined in claim 15, wherein the sampling tool includes a shaft extending from the base of the tool head, and a sample removing means slidably mounted on the shaft, the sample removing means having a front face shaped to complement the base of the tool head and able to engage the base of the tool head to squeeze the sample away from the base.

18. A sampling tool as defined in claim 16, wherein the sampling tool includes a shaft extending from the base of the tool head, and a sample removing means slidably mounted on the shaft, the sample removing means having a front face shaped to complement the base of the tool head and able to engage the base of the tool head to squeeze the sample away from the base.

19. A sampling tool as defined in claim 17, wherein the sample removing means includes a cutting edge facing the base of the tool head so as to be able to cut sinew or gristle encircling the shaft between the sample removing means and the base of the tool head.

\* \* \* \* \*